(12) United States Patent
Rangayyan et al.

(10) Patent No.: US 6,537,233 B1
(45) Date of Patent: Mar. 25, 2003

(54) AUDITORY DISPLAY OF KNEE JOINT VIBRATION SIGNALS

(75) Inventors: Rangaraj M. Rangayyan, Calgary (CA); Sridhar Krishnan, Calgary (CA); Douglas B. Bell, Calgary (CA); Cyril B. Frank, Calgary (CA)

(73) Assignee: University Technologies International Inc., Calgary (CA)

( * ) Notice: Subject to any disclaimer, the term of this patent is extended or adjusted under 35 U.S.C. 154(b) by 130 days.

(21) Appl. No.: 09/706,987

(22) Filed: Nov. 6, 2000

(51) Int. Cl.$^7$ .................................................. A61B 7/00
(52) U.S. Cl. ........................ 600/586; 600/587; 600/595; 600/300
(58) Field of Search ................................. 600/586, 587, 600/595, 300, 483, 528; 346/33 R, 33 ME; 604/19, 22

(56) References Cited

U.S. PATENT DOCUMENTS

| | | | |
|---|---|---|---|
| 3,181,528 A | | 5/1965 | Brackin |
| 4,437,473 A | | 3/1984 | Mollan |
| 4,543,957 A | * | 10/1985 | Friedman et al. ........... 600/300 |
| 4,802,484 A | * | 2/1989 | Friedman et al. ........... 600/300 |
| 4,823,807 A | | 4/1989 | Russell et al. |
| 4,836,218 A | | 6/1989 | Gay et al. |
| 4,991,581 A | * | 2/1991 | Andries ...................... 600/528 |
| 5,031,637 A | * | 7/1991 | Parra .......................... 600/586 |
| 5,137,029 A | * | 8/1992 | Parra .......................... 600/586 |
| 5,255,685 A | * | 10/1993 | Parra .......................... 600/483 |
| 5,533,519 A | | 7/1996 | Radke et al. |
| 5,810,747 A | * | 9/1998 | Brudny et al. .............. 600/595 |
| 6,159,166 A | * | 12/2000 | Chesney et al. ............ 600/586 |

OTHER PUBLICATIONS

"Analysis of Knee Joint Sound Signals for Non–Invasive Diagnosis of Cartilage Pathology" R. M. Rangayyan, et al, Mar., 1990 IEEE.

"Adaptive Filtering, modelling and classification of knee joint vibroarthrographic signals for non–invasive diagnosis of articular cartilage pathology", R.M. Rangayyan, et al. Nov. 1997.

"Parametric Representation and Screening of Knee Joint Vibroarthrographic Signals", R.M. Ranagyyan et al., 1997 IEEE.

"Time–Frequency Signal Feature Extraction and Screening of Knee Joint Vibroarthrographic Signals Using The Matching Pursuit Method", R.M. Rangayyan, et al., Oct. 1997.

"Comparative Analysis of the Performance of the Time–Frequency Distributions with Knee Joint Vibroarthrographic Signals", R.M. Rangayyan, et al., Oct. 1998.

"Detection of Nonlinear Frequency–Modulated Components in the Time–Frequency Plane Using An Array of Accumulators", R.M. Rangayyan, et al., Oct., 1998.

"Detection of Chirp and Other Components in the Time-–Frequency Plane using the Hough and Radon Transforms", R.M. Rangayyan, et al., 1997 IEEE.

"Feature Identification in Time–Frequency Distributions of Knee Joint Vibration Signals Using the Hough–Radon Transform", R.M. Rangayyan, et al. Jul. 16–18, 1999.

* cited by examiner

Primary Examiner—Teresa Walberg
Assistant Examiner—Fadi H. Dahbour
(74) Attorney, Agent, or Firm—Bennett Jones LLP

(57) ABSTRACT

Computer-assisted auscultation of knee joints by auditory display of vibroarthrographic signals emitted during active movement of the leg include audification and sonification. In audification, the vibroarthrographic signals are scaled in time and frequency using a time-frequency distribution to facilitate aural analysis. In sonification, the instantaneous mean frequency and envelope of the vibroarthrographic signals are derived and used to synthesize sounds that may facilitate more accurate diagnosis than the original signals by improving their aural quality.

9 Claims, 7 Drawing Sheets

AUDITORY DISPLAY OF KNEE JOINT VIBRATION SIGNALS

FIELD OF THE INVENTION

The present invention relates to non-invasive methods of analyzing vibration signals from a joint by auditory display of the vibration signals. The present invention may be adapted for use with any joint in a human or animal body but is particularly useful for diagnosing disorders in a human knee joint.

BACKGROUND OF THE INVENTION

Auscultation, the method of examining functions and conditions of physiological systems by listening to the sounds they produce, is one of the ancient modes of diagnosis. The first use of vibration or acoustic emission as a diagnostic aid for bone and joint disease is found in Laennec's treatise on auscultation, cited by Mollan et al. [1]. Laennec was able to diagnose fractures by auscultating crepitus caused by the moving broken ends of bone. Heuter, in 1885, used a myodermato-osteophone, a type of stethoscope, to localize loose bodies in human knee joints. [1]. In 1929, Walters reported on auscultation of 1600 joints and detected certain sounds before symptoms become apparent [2]; he suggested that the sounds might be an early sign of arthritis.

After 1933, most of the works reported on knee-joint sounds have been on objective analysis of the sound or vibration signals, also known as vibroarthrographic (VAG) signals, for noninvasive diagnosis of knee-joint pathology [3, 4, 5, 6, 7, 8, 9 10, 11]. Although auscultation of knee joints using stethoscopes is occasionally practised by clinicians, there is no published evidence of their diagnostic value. Also, there has been no published report on computer-aided auscultation of knee-joint sounds.

Prior to graphical recording and analysis of VAG signals, auscultation of knee joints was the only noninvasive method available to distinguish normal joints from degenerative joints. Significant success has been claimed by several researchers using the auscultation technique. However, classification of knee joints by auscultation is a highly subjective technique. Further, a significant portion of the VAG signal energy lies below the threshold of auditory perception of the human ear in terms of frequency and/or intensity.

VAG signals from knee joints lie at the lower end of the frequency spectrum and the audible sound is only a part of the total vibration spectrum. The presence of background noise, muscle vibration artifacts and the complex nature of the VAG signal makes auscultation very difficult. As well, clicks of clinical interest are of short duration and direct auscultation cannot detect subtle changes or differences in such transients.

Auditory display techniques may be useful to facilitate auscultation of knee joint and other joints. Auditory display may be defined as an aural representation of a stream of data.

Therefore, there is a need in the art for methods for computer-aided auscultation of joint sounds based on auditory display (AD) techniques.

BRIEF DESCRIPTION OF THE DRAWINGS

The invention will now be described by way of exemplary embodiments with reference to the following drawings in which.

DESCRIPTION OF THE INVENTION

Figure 1:
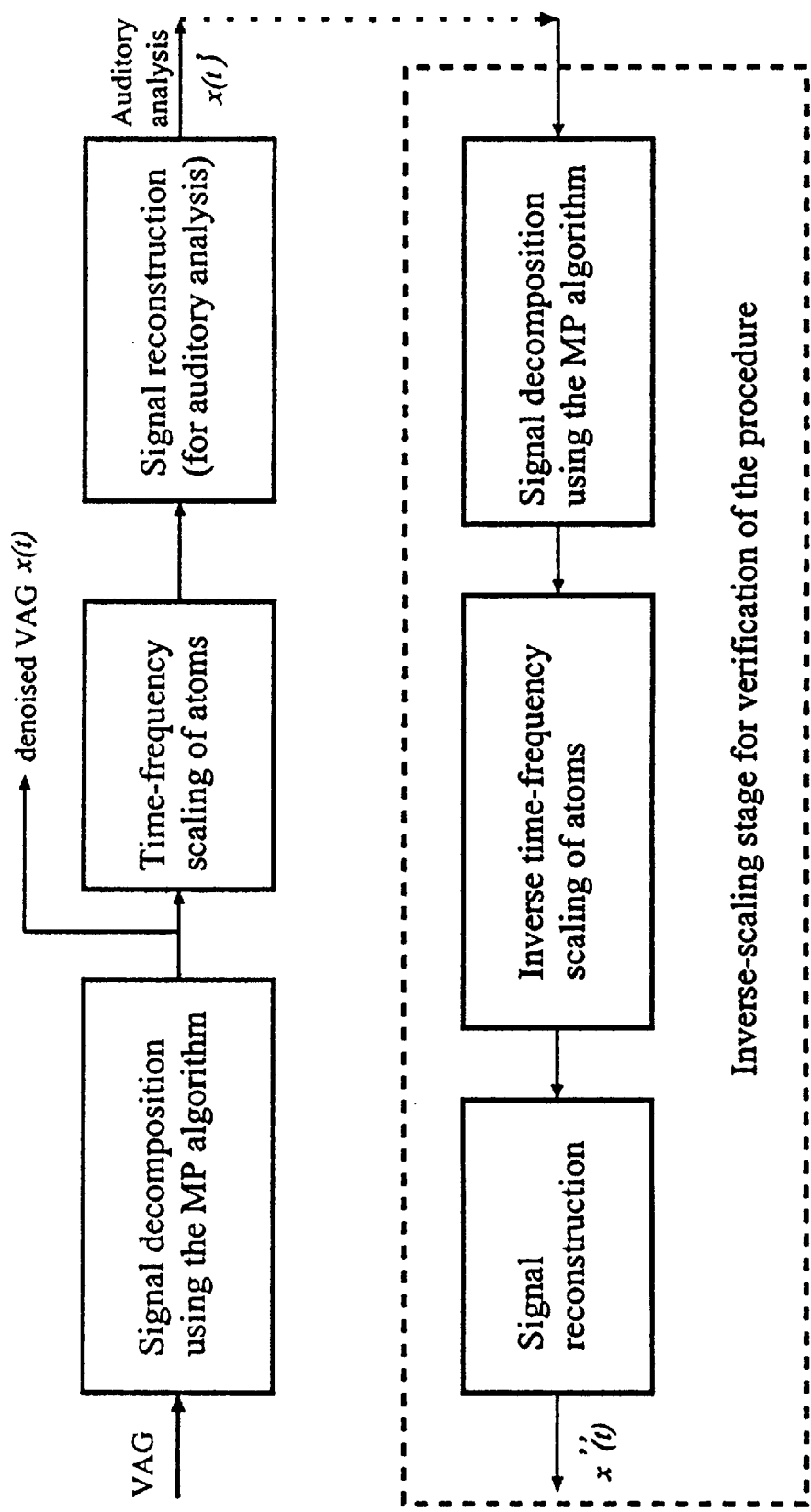
FIG. 1 is a schematic block diagram of a matching pursuit based audification method of the present invention.

The present invention provides for methods of non-invasively diagnosing abnormal joint conditions by the auditory display of a VAG signal. In particular, the methods described herein are useful for diagnosing the quality of articular cartilage in a knee joint. However, it is not intended to limit the claimed invention to one specific application. The claimed invention may be applicable to the diagnosis of a wide variety of conditions where auscultation is a diagnostic tool.

When describing the present invention, the following terms have the following meanings, unless indicated otherwise. All terms not defined herein have their common art-recognized meanings.

The term "vibroarthrographic signal" refers to an electronically recorded signal that represents the sound or noise or vibration generated in or by a joint of a body. The signal may be sensed using a microphone, accelerometer or a vibration sensor, which are all well known in the art.

1. Auditory Display

Auditory display may be defined as an aural representation of a stream of data. In general terms, the invention comprises the audification or sonification of a VAG signal obtained from a knee joint.

1.1 Audification

Audification is the direct transformation of a data stream to the audible domain for purposes of monitoring and analysis. Filters and signal processing techniques may be used to assist the user of the display in isolating certain events, but there are no sound-synthesizing elements involved.

The audification of VAG signals may be performed in two ways: 1) direct playback, 2) audification via a time-frequency scaling method based on a signal decomposition technique such as matching pursuit (MP) [11, 21].

1.1.1 Direct Playback

In direct playback, the digitized VAG signals may be converted to an audio file and replayed using audio software tools which are well known. In one embodiment, the audio file (.au) format is that played using the "audiotool" program in an Ultraspare (SUN Microsystems) station. Direct playback of VAG signals may provide more information than the sounds heard using a stethoscope due to better noise immunity, sensitivity, and low-frequency response of an accelerometer than a stethoscope.

1.1.2 MP-based Audification

VAG signals lie at the lower end of the frequency spectrum, and audible sound is only a part of their total spectral content. The presence of background noise, muscle vibration artifacts, and the complex nature of the VAG signal make auscultation difficult. A technique that shifts the frequency spectrum of components of diagnostic relevance to a higher and more easily perceptible range may be useful. On the other hand, clicks of clinical interest are of very short duration, and direct auscultation or direct audification may not facilitate auditory analysis of the subtle characteristics of such transients. A method that scales transients to a longer duration may facilitate improved auscultation.

In one embodiment, time-frequency (TF) scaling is performed using the method proposed by Zhang et al. [13] for heart sounds. The method is based on MP decomposition, and the atoms generated as a result of the decomposition procedure are suitably time-scaled and frequency-scaled. The scaled atoms are used in the synthesis stage to construct a TF-scaled signal.

FIG. 1 shows the block diagram of the MP-based audification method. The original VAG signal is decomposed into TF atoms by using the MP method described below. The MP decomposition process is stopped once the coherent structures of the signal are extracted. At the decomposition stage, the MP algorithm provides the parameters $\alpha_n$, $s_n$, $p_n$, $f_n$ and $\phi_n$ in Eq.7 below. By scaling t, $s_n$, and $p_n$ a time-scaled version of the signal can be obtained. Scaling $f_n$ gives a frequency-scaled version of the signal. The scaling parameters can be varied suitably to obtain the desired perceptual, frequency, and temporal characteristics.

In joint TF scaling, the time (t) and the frequency ($f_n$) variables are transformed to new variables t' and $f'_n$, respectively, by the scalar transformations $$t' = \alpha t \qquad (1)$$

$$f'_n = \beta f_n \qquad (2)$$

where $\alpha$ and $\beta$ are positive numbers. $\alpha > 1$ expands the signal in time, and $\alpha < 1$ compresses the signal in time without any change in the spectral characteristics. $\beta > 1$ shifts the spectral bandwidth to a higher frequency range and $\beta < 1$ shifts the spectral bandwidth to a lower frequency range; the frequency transformation does not affect the temporal properties. In case of critically-sampled signals, the following condition should be met:

$$f_s! \geq 2\beta f_m, \qquad (3)$$

where $f_n$ is the maximum frequency component present in the signal, and $f_s$ is the sampling rate. The condition in Eq. 3 avoids frequency aliasing in frequency-scaled versions of the signals.

In the present application, we are interested in playing VAG signals for a longer duration with frequency mapping to an audible band in a comfortable frequency range for human perception. The temporal properties of the signal are related to the time-position $p_n$, and the scale factor $s_n$. Therefore, in the time-scaling procedure, the temporal placement and the scale factors are transformed to p'$_n$, and s'$_n$, where p'$_n$=$\alpha$p$_n$ and s'$_n$=$\alpha$s$_n$. In case of frequency scaling, the frequency variable $f_n$ is transformed to $f'_n$=$\beta f_n$.

The TF-scaled atom is given by $$g'_{\gamma_n}(t) = \frac{1}{\sqrt{s'_n}} g\left(\frac{t - p'_n}{s_n}\right) \exp[j(2\pi f'_n \alpha t + \phi_n]  \qquad (4)$$

$$= \frac{1}{\sqrt{\alpha \gamma_n}} g\left(\frac{t' - \alpha \phi_n}{\alpha \gamma_n}\right) \exp[j(2\pi \beta f_n \alpha t + \phi_n]$$

From Eq. 4 it is evident that in time-scaling, the spectral characteristics remain unchanged. Normally, a time-scale expansion by a factor of $\alpha$ decreases the rate (frequency) by $1/\alpha$. By introducing $\alpha$ in the phasor part of the expression in Eq. 4, the original rate of the signal is maintained; in other words, the frequency characteristics remain unchanged with time-scale expansion (or contraction).

MP reconstruction using the TF-scaled atoms provides the desired TF-scaled signal x(t'), which may be expressed as $$x(t') = \sum_{n=0}^{M-1} a_n g_{\gamma'_n}(t'), \qquad (5)$$

where M is the total number of coherent TF structures provided by MP decomposition.

The inverse TF scaling part shown in FIG. 1 is preferred, but not essential, in order to verify the scaling procedures. After TF scaling, the temporal and/or spectral properties of the signals are changed, and verification of the scaling process becomes difficult. Therefore, for quantitative evaluation of the scaling process, an inverse scaling procedure was also implemented, where the variable t' and $f'$ are transformed back to t and $f$, by using the scale parameters $1/\alpha$ and $1/\beta$, respectively. If there is no distortion caused by the scaling transformations and the MP decomposition procedures, the denoised signal x(t) and the inverse-scaled signal x"(t) should be identical.

1.2 Time-Frequency Distributions (TFDs)

We have observed that because of certain characteristics of VAG signals, they cannot be easily analyzed by common signal processing techniques such as the Fourier transform. Techniques such as autoregressive modeling cannot accurately characterize a nonstationary signal like a VAG signal. We have found that a nonstationary signal analysis tool such as a joint time-frequency distribution (TFD) may be used.

A preferred TFD for VAG signals may be one that can give an accurate display of VAG characteristics with reasonable TF resolution and cross-term suppression, and can emphasize in the TF plane the expected characteristics of VAG signals. A preferred TFD may be utilized in feature extraction and identification methods.

1.2.1 Preferred Characteristics of TFDs

If x(t) is a signal and TFD (t,$\omega$) is its joint TFD, then the following are criteria that the TFD preferably, but not necessarily, should satisfy [23]:

Total Energy: $\int\int TFD(t,\omega)dtd\omega = \int |x(t)|^2 dt = \int |X(\omega)|^2 dw$ where X($\omega$) is the Fourier transform of (x)t. This criterion indicates that at a particular t and $\omega$, TFD (t,$\omega$) gives the fractional energy of the signal. Further, TFD (t,$\omega$) may be viewed as a two-dimensional probability density function (PDF), with t and $\omega$ considered to be random variables.

Invariance: The TFD should be invariant to linear shifts in time and frequency. In most cases it is also expected that the TFD is scale-invariant. The invariance criterion helps in understanding the TF localization, and helps in extracting meaningful features.

Positivity: For a TFD to be positive, it is required that TFD (t,ω)>0 for all t and ω. The positivity criterion helps in treating the TFD as a PDF. If a TFD possesses negative values, it could pose severe interpretation problems and may not be suitable for objective feature extraction and identification purposes.

Marginals: The interpretation of TFDs as PDFs help in extracting the marginal distributions by integrating either in the time or frequency direction. Integration along frequency gives the instantaneous energy of the signal:
∫TFD(t,ω)dw=|x(t)|². Integration along time gives the power spectral density of the signal: ∫TFD(t,ω)dt= |X(ω)|².

Global Expectation Values: Global expectation values may give an idea about signal behaviour at a particular time and frequency.
E{g(t,ω)}=∫∫g(t,ω)TFD(t,ω)dtdω. E{g(t,ω)} expresses a generalized moment of a TFD. The function g(t,ω) is chosen according to the desired moment.

Local Expectation Values; Local expectation values may be obtained by applying the expectation operator with respect to time or frequency, and help in tracking non-stationary features such as instantaneous frequency and group delay of a signal. The instantaneous mean frequency is given by the time-varying first moment of the TFD along frequency.

$$E_t\{\omega\} = \frac{1}{|x(l)|^2}\int \omega TFD(t,\omega)d\omega.$$

The group delay is given as the frequency varying first moment of the TFD along time $$E_\omega\{t\} = \frac{1}{|X(\omega)|^2}\int lTFD(t,\omega)dt.$$

The group delay yields the mean time of arrival for a given frequency.

Finite Support: If x(t) is zero at $t_1$, then TFD($f_1$, ω) should be zero. Also if X(ω) is zero at $\omega_1$, then TFD(t,$\omega_1$) should be zero.

The simplest of all TFDs is the spectrogram. The spectrogram of a signal is computed as the squared modulus of its short-time Fourier transform (STFT). Spectrograms have inherent trade-off between time and frequency resolution, and do not satisfy the marginal and finite-support criteria. These shortcomings restrict application of the spectrogram as a TFD tool for VAG signal analysis. Among the other types of TFDs available, the Cohen's class of bilinear TFDs have received significant attention in signal analysis [23]. Cohen's class distributions are quadratic in nature. Quadratic distributions have to perform a trade-off between joint TF resolution and the level of cross-terms. Objective and subjective analysis of TFDs indicate that Cohen's class of bilinear TFDs are not preferred for VAG signal extraction [22].

1.2.1 Adaptive TFDs

It is widely accepted that, in the case of complex signals where objective feature extraction is desired, there is no definite TFD that will satisfy all the criteria and still give optimal performance. The purpose of the methods described in this section is to construct TFDs according to the properties of the signal being analyzed. Such TFDs may be referred to as adaptive TFDs and may provide preferred TFDs for the sonification method referred to herein.

Figure 3:
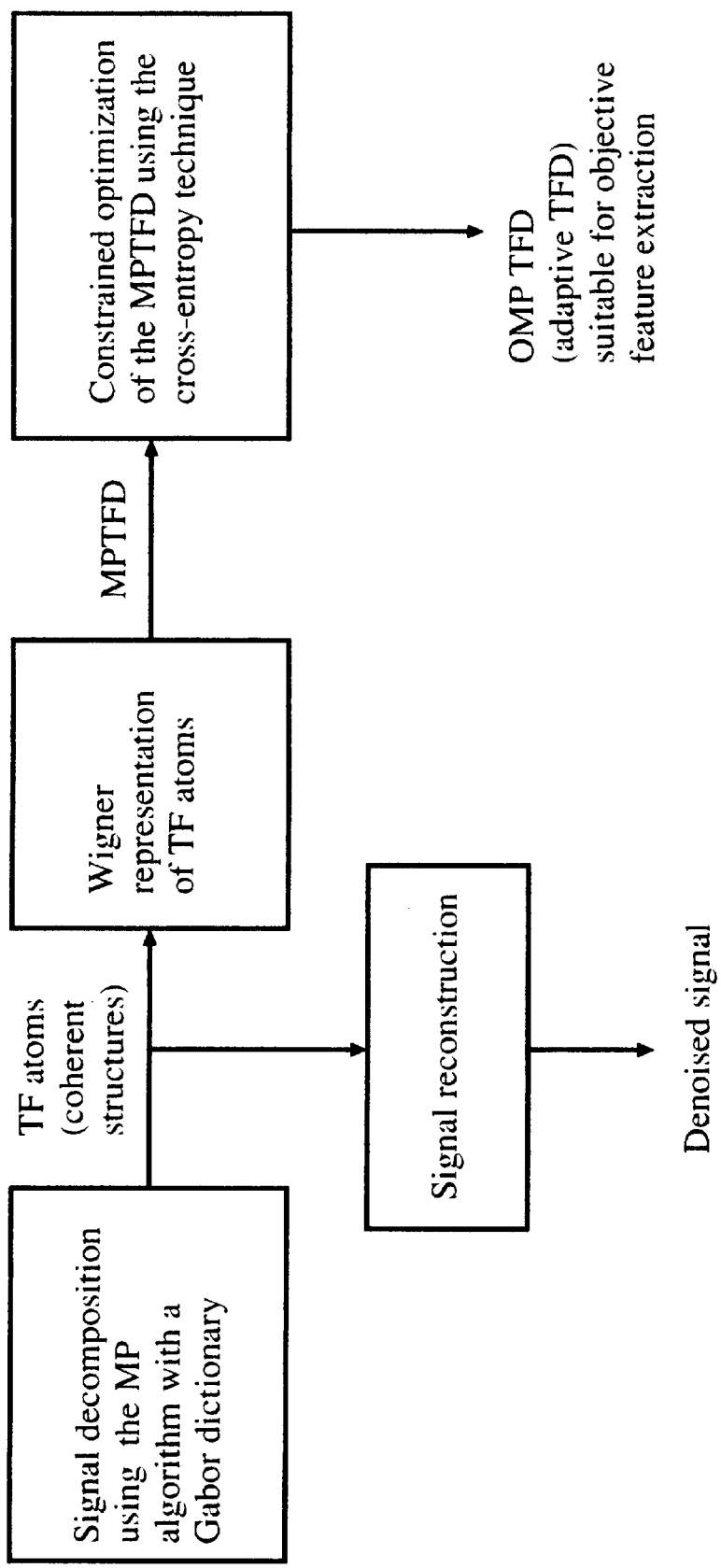
FIG. 3 is a schematic block diagram of a method for constructing an adaptive time-frequency distribution.

In one embodiment, the concept of adaptive TFDs is based on signal decomposition. A block diagram of a method for adaptive TFD construction is shown in FIG. 3. It is assumed that the given signal is somehow decomposed into components of a specified mathematical representation. By knowing the components of the signal, the interation between them can be established and used to remove or prevent cross-terms. This avoids the main drawback associated with Cohen's class TFDs for which numerous efforts have been directed to develop kernels to overcome the cross-term problem.

The components obtained from a decomposition algorithm depend largely on the type of basis functions used. In one example, the basis function of the Fourier transform decomposes the signal into tonal (sinusoidal) components, and the basis function of the wavelet transform decomposes the signal into components with good time and scale properties. For TF representation, it preferred if the signal is decomposed using basis functions with good TF properties. The MP algorithm described below can suitably decompose a signal into TF atoms.

1.2.2 Matching Pursuit Signal Decomposition

Matching pursuit (MP) is a signal decomposition algorithm that decomposes a given signal using basis functions that have excellent TF properties. The MP algorithm selects the decomposition vectors depending upon the signal's properties. The vectors are selected from a family of waveforms called a dictionary. The signal x(t) is projected onto a dictionary of TF atoms obtained by scaling, translating and modulating a window function g(t):

$$x(t) = \sum_{n=0}^{\infty} a_n g_{\gamma n}(t), \quad (6)$$

where $$g_{\gamma n}(t) = \frac{1}{\sqrt{s_n}} g\left(\frac{t - p_n}{s_n}\right) \exp[j(2\pi f_n t + \phi_n] \quad (7)$$

and $\alpha_n$ are the expansion coefficients. The scale factor $s_n$ is used to control the width of the window function, and the parameter $p_n$ controls temporal placement.

$$\frac{1}{\sqrt{s_n}}$$

is a normalizing factor that restricts the norm of $g_{\gamma n}$ (t) to 1. $\gamma_n$ represents the set of parameters ($s_n$, $p_n$, $f_n$, $\phi_n$). In the present invention, the window is a Gaussian function, i.e. g(t)=$2^{1/4}$ exp($-\pi t^2$); the TF atoms are then Gabor atoms.

In practice, the algorithm works as follows. The signal is iteratively projected onto a Gabor function dictionary. The first projection decomposes the signal into two parts:

$$x(t)=(x,g_{\gamma 0})g_{\gamma 0}(t)+R^1x(t) \quad (8)$$

where (x,$g_{\gamma 0}$) denotes the inner product (projection) of x(t) with the first TF atom $g_{\gamma 0}$(t). The term $R^1$x(t) is the residue after approximating x(t) in the direction of $g_{\gamma 0}(t)$. This process is continued by projecting the residue onto the subsequent functions in the dictionary, and after M iterations $$x(t) = \sum_{n=0}^{M-1} \langle R^n x, g_{\gamma n} \rangle g_{\gamma n}(t) + R^M x(t), \quad (9)$$

where $R^0 x(t) = x(t)$. There are two ways of stopping the iterative process: one is to use a prespecified limiting number M of the TF atoms, and the other is to check the energy of the residue $R^M x(t)$. A very high value of M and a zero value for the residual energy will decompose the signal completely at the expense of increased computational complexity. In one embodiment, decomposition is stopped after extracting the first M coherent structures of the signal, determined using a decay parameter [21].

$$\lambda(m) = \sqrt{1 - \frac{\|R^m x\|^2}{\|R^{m-1} x\|^2}} \quad (10)$$

in Eq. 10, $\|R^M x\|^2$ denotes the residual energy at the mth iteration. The decomposition is continued until the decay parameter does not reduce any further. At this stage, the selected components represent the coherent structures and the residue represents the incoherent structures in the signal with respect to the dictionary. The residue may be assumed to be due to random noise, since it does not show any TF localization. The signal reconstructed using the M coherent structures extracted, i.e., $$x(t) = \sum_{n=0}^{M-1} \langle R^n x, g_{\gamma n} \rangle g_{\gamma n}(t), \quad (11)$$

provides the MP-denoised version of the original [11,29].

1.3 Matching Pursuit Time-Frequency Distributions (MPTFDs)

A signal-decomposition based TFD may be obtained by taking the Wigner-Ville distribution (WVD) of the TF atoms obtained from the MP algorithm (11) and is given as $$W(t, \omega) = \sum_{n=0}^{M-1} |\langle R^n x, g_{\gamma n} \rangle|^2 W g_{\gamma n}(t, \omega) + \sum_{\substack{n=0 \\ n \neq 11}}^{M-1} \sum_{\substack{m=11}}^{M-1} \langle R^n x, g_{\gamma n} \rangle \langle R^m x, g_{\gamma m} \rangle^* \times W_{[g_{\gamma n}, g_{\gamma m}]}(t, \omega) \quad (25)$$

where $Wg_{\gamma n}(t,\omega)$ is the WVD of the Gaussian window function. The double sum corresponds to the cross-terms of the WVD indicated by $W_{[g_{\gamma n}, g_{\gamma n}]}(t,\omega)$ and should be rejected in order to obtain a cross-term free energy distribution of x(t) in the TF plane.

Thus, only the first term is retained, and the resulting TFD is given by $$W'(t, \omega) = \sum_{n=0}^{M-1} |\langle R^n x, g_{\gamma n} \rangle|^2 W g_{\gamma n}(t, \omega) \quad (26)$$

This cross-term free TFD, referred to herein as the matching pursuit TFD (MPTFD), has very good readability and is preferred for analysis of nonstationary, multicomponent signals such as VAG signals from knee joints. The extraction of coherent structures makes MP a preferred tool for TF representation of signals with unknown SNR.

1.4 Minimum Cross-Entropy Optimization of the MPTFD

One of the drawbacks of the MPTFD is that it does not satisfy the marginal properties. The MPTFD may be modified to satisfy the marginal requirements, and still preserve its other important characteristics. One way to optimize the MPTFD is by using the cross-entropy minimization method [23, 24]. Cross-entropy minimization is a general method of inference about an unknown probability density function (PDF) when there exists a prior estimate of the function and new information in the form of constraints on expected values is available. If the optimized MPTFD or OMP TFD (an unknown PDF) is denoted by M(t,), then it should satisfy the marginals.

$$\int M(t, 107) d\omega = |x(t)|^2 = m(t) \quad (12)$$

and $$\int M(t,\omega) dt = |X(\omega)|^2 = m(\omega) \quad (13)$$

Equations (12) and (13) may be treated as constraint equations (new information) for optimization. Now, M(t,) may be obtained from W'(t,) (a prior estimate of the function) by minimizing the cross-entropy between them, given by $$H(M, W') = \int \int M(t, \omega) \log\left(\frac{M(t, \omega)}{W'(t, \omega)}\right) dt d\omega. \quad (14)$$

As we are interested only in the marginals, the OMP TFD may be written as [24]

$$M(t,\omega) = W(t,\omega) \exp\{-[\alpha_0(t) + \beta_0(\omega)]\} \quad (15)$$

where the $\alpha$'s and $\beta$'s are Lagrange multipliers which may be determined using the constraint equations. An iterative algorithm to obtain the Lagrange multipliers and solve for M(t,ω) is presented next.

At the first iteration, we define $$M^1(t,\omega) = W(t,\omega) \exp[-\alpha_0(t)] \quad (16)$$

As the marginals are to be satisfied, the time marginal constraint has to be imposed in order to solve for $\alpha_n(t)$. By imposing the time marginal constraint given by (12) on (16), we obtain $$\alpha_0(t) = \ln\left(\frac{m'(t)}{m(t)}\right) \quad (17)$$

where m(t) is the desired time marginal and m'(t) is the time marginal estimated from W'(t,ω).

Now, Eq. (16) can be written as $$M^1(t, \omega) = W'(t, \omega) \frac{m(t)}{m'(t)} \quad (18)$$

At this point, $M^1(t,\omega)$ is a modified MPTFD with the desired time marginal; however, it may not necessarily have the desired frequency marginal m(ω). In order to obtain the desired frequency marginal, the following equation has to be solved:

$$M^2(t,\omega)=M^1(t,\omega)exp[-\beta_0(\omega)] \quad (19)$$

Note that the TFD obtained after the first iteration $M^1(t,\omega)$ is used as the incoming estimate in (19). By imposing the frequency marginal constraint given by (13) on (19), we obtain $$\beta_0(\omega) = \ln\left(\frac{m'(\omega)}{m(\omega)}\right) \quad (20)$$

where $m(\omega)$ is the desired frequency marginal, and $m'(\omega)$ is the frequency marginal estimated from $W'(t,\omega)$. Now, (20) can be rewritten as $$M^2(t,\omega) = M^1(t,\omega)\frac{m(\omega)}{m'(\omega)} \quad (21)$$

By incorporating the desired marginal constraint, the $M^2(t,\omega)$ TFD may be altered and may not necessarily give the desired time marginal. Successive iteration could overcome this problem and modify the desired TFD to get closer to $M(t,\omega)$. This follows from the fact that the cross-entropy between the desired TFD and the estimated TFD decreases with the number of iterations [24].

As the iterative procedure is started with a positive distribution $W'(t,\omega)$, the TFD at the nth iteration $M^n(t,\omega)$ is guaranteed to be a positive distribution. Such a class of distributions belongs to the Cohen-Posch class of positive distributions [22]. The OMP TFDs are adaptive TFDs because they are constructed on the basis of the properties of the signal being analyzed.

A method for constructing a positive distribution using a spectrogram as a priori knowledge was developed by Loughlin et al. [30]. The major drawback of using the spectrogram as a priori knowledge is the loss of TF resolution: this effect may be minimized by taking multiple spectrograms with analysis windows of different sizes as initial estimates of the desired distribution. The method proposed herein starts with the MPTFD, overcomes the problem of using multiple spectrograms as initial estimates, and produces a high-resolution TFD tailored to the characteristics of the signal at hand.

1.5 Sonification of VAG Signals

Figure 2:
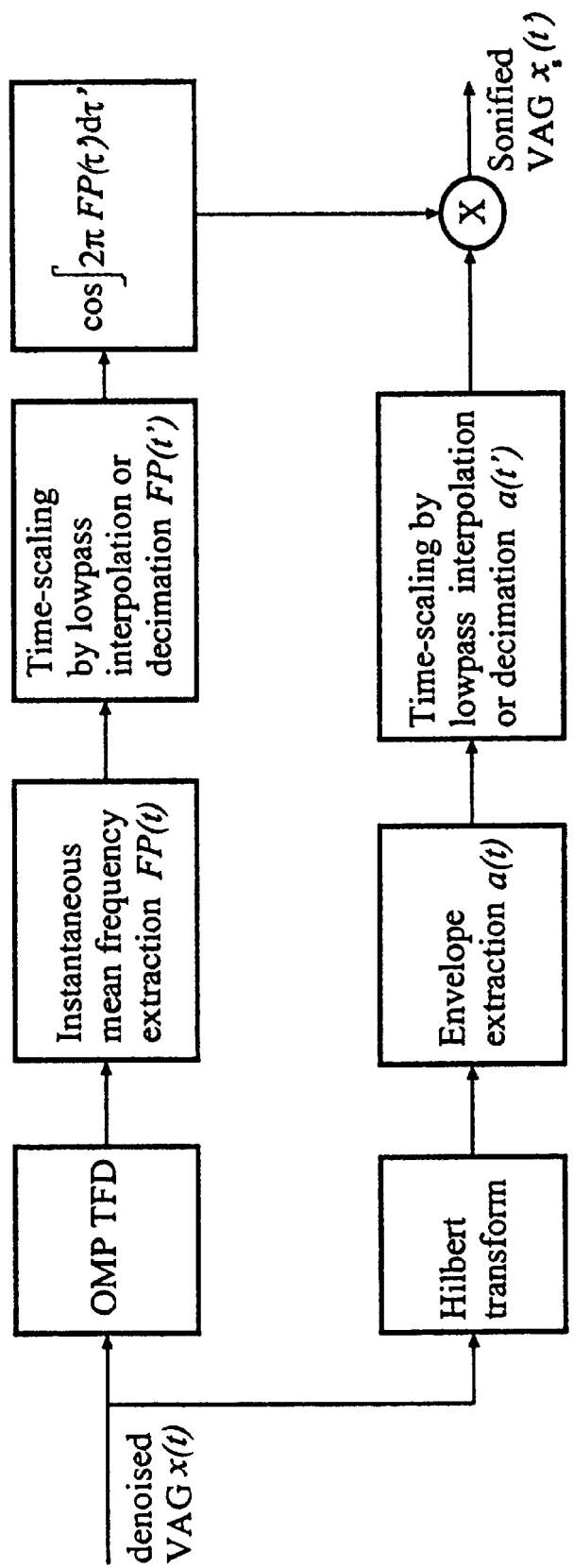
FIG. 2 is a schematic block diagram of an instantaneous mean frequency based sonification method of the present invention.

It is known that VAG signals are multicomponent signals [11]. Hence, in TF scaling, shifting all the components of a VAG signal to a different frequency band may not bring out the event of interest, and may obscure the features of diagnostic value. In an effort to facilitate AD of only the important characteristics of VAG signals, a sonification algorithm is proposed. A block diagram of the proposed sonification method is shown in FIG. 2.

In sonification, features extracted from the data are used to control a sound synthesizer. The sound signal generated does not bear a direct relationship to the original data. A simple example of a sonification technique is mapping of parameters derived from a data stream to AD parameters such as pitch and loudness.

The sonification algorithm involves amplitude modulation (AM) and frequency modulation (FM). The instantaneous mean frequency (IMF) of a signal is an important parameter in characterizing multicomponent, nonstationary signals such as a VAG signal [22]. The FM part of the sonified signal is obtained by frequency-modulating a sinusoidal waveform with the IMF of the signal. The auditory characteristics of the FM part alone will be tonal, which could quickly cause boredom and fatigue. To obviate this problem, an AM part is obtained as the absolute value of the analytic version of the VAG signal. The AM part provides an envelope to the signal and frequency deviation (bandwidth) about the IMF. The IMF-based sonification algorithm is summarized as follows:

1. Construct a positive TFD [23, 11], preferably an MPTFD or an OPM TFD, of the signal.
2. Extract the IMF (frequency parameter FP(t)) as the first central moment of the TFD along the frequency axis.
3. Lowpass-interpolate the FP(t) waveform by the required time-scale factor; that is, obtain FP(t'), where $t'=\alpha t$.
4. Take the Hilbert transform of the denoised VAG signal and form its analytic representation as $$\alpha(t)=x(t)+jH\{x(t)\} \quad (22)$$

where $H\{.\}$ is the Hilbert transform.

5. Extract the envelope of the signal by taking the magnitude of $\alpha(t)$, i.e., $$|\alpha(t)|=\sqrt{x^2(t)+(H\{x(t)\})^2}. \quad (23)$$

6. Lowpass-interpolate the envelope by the required time-scale factor; that is, obtain $\alpha(t')$.
7. Construct the sonified signal $x_s(t')$ by combining the envelope and the IMF components, i.e., $$x_s(t')=|\alpha(t')| \cos (\int_{-\infty}^{t'} 2\pi FP(\tau')d\tau'+\phi_0), \quad (24)$$

where $\phi_0$ is an arbitrary phase constant. The derivative of the phase of $\alpha(t)$ may be used to extract the IMF of the signal. Extensive research has been conducted on the extraction of the IMF of a signal via the phase of its analytic form [24, 25, 23, 26]. However, it has been observed that the IMF extracted via the phase of the analytic signal often leads to paradoxical results such as the IMF taking negative and non-interpretable values [25, 26, 27]. The approach of using TFDs to extract the IMF provides an interpretable value that is always positive [23, 11].

The advantages of the IMF-based sonification method are:

It helps in auditory analysis of a multicomponent nonstationary signal in terms of its main features such as FP(t) and $\alpha(t)$.

FP(t) takes high values for transients and noise. However, by making use of the envelope (intensity) information, noise can be made less audible as compared to transients.

If FP(t) is in the subaudible range, it can be shifted to the audible band by frequency scaling. Frequency scaling can be easily achieved by just multiplying FP(t) by the required frequency scale factor $\beta$; that is, FP'(t)=$\beta$FP(t).

Integration of FP(t) ensures a continuous phase, and the method does not require any phase unwrapping.

Integration of FP(t) makes the method insensitive to noisy FP(t) estimates.

In the case of a noisy signal, FP(t) will have an almost uniform waveform, and does not provide much information unless the envelope can contribute some information. In the present study, this problem is overcome by processing denoised versions of the VAG signals.

It is obvious that the sonification method of the present invention may not be applicable to information-rich signals such as speech: the formant structure of voiced speech cannot be represented by the relatively simple IMF. For AD of signals with rich spectral information, audification might be the better choice.

2. Examples

2.1 Data Acquisition

Test subjects sat on a rigid table in a relaxed position with the leg being tested freely suspended in air. The VAG signal was detected on the skin surface at the mid-patella position of the knee by using vibration sensors (Dytran 3115a accelerometers) as the subject swung the leg over an approximate angle range of 135°→0°→135° in 4s.

The VAG signal was prefiltered by a bandpass filter of bandwidth 10 Hz to 1 kHz and amplified using isolation pre-amplifiers (Gould, Cleveland, Ohio, model 11-5407-58) and universal amplifiers (Gould, model 13-4615-18) before digitizing. A data acquisition board (National Instruments, Austin, Tex., AT-MIO-16L) and Lab Windows software (National Instruments) were used to digitize the signals at a sampling rate of 2 kHz and 12 bits per sample. Details of data acquisition may be found in Krishnan et al. [9].

Figure 4:
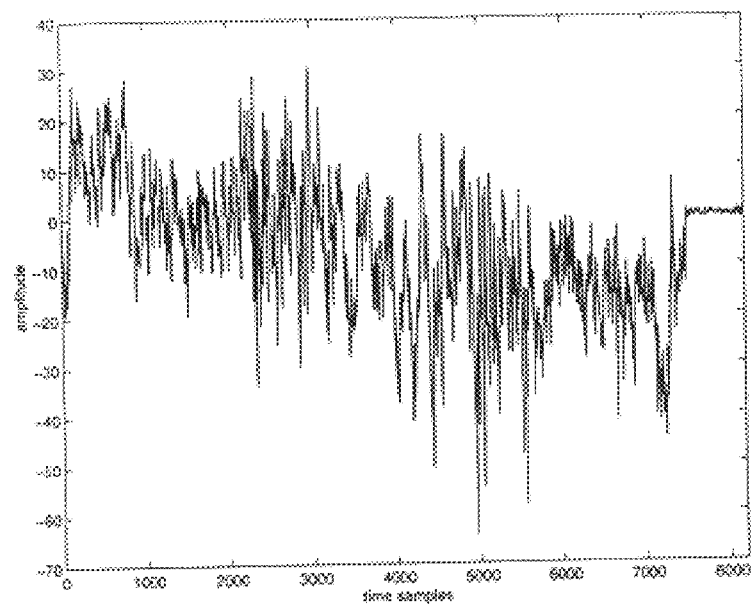
FIG. 4 is a VAG signal of a person with chondromalacia Grade II and III.
Figure 5:
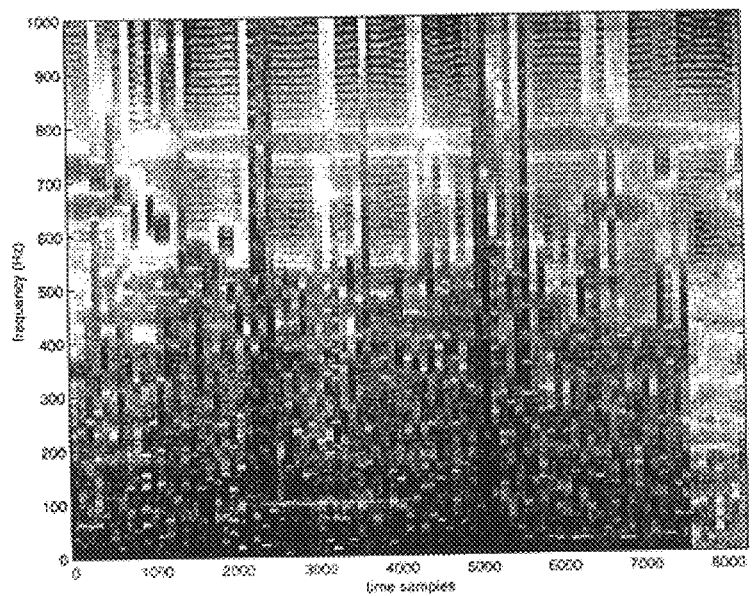
FIG. 5 is a spectrogram of the VAG signal shown in FIG. 4.
Figure 6:
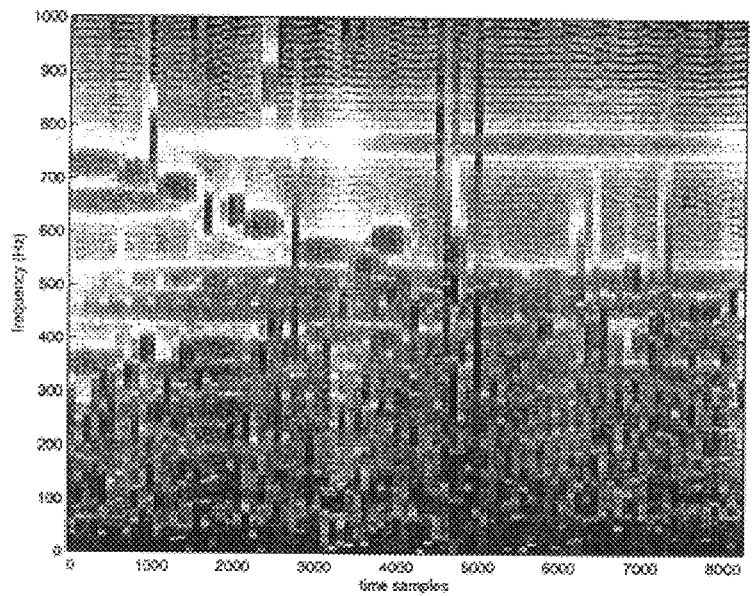
FIG. 6 is a spectrogram of the MP-based audified version of the VAG signal shown in FIG. 4. The figure window has been divided into 2 parts to show the time-scale expansion.
Figure 6:
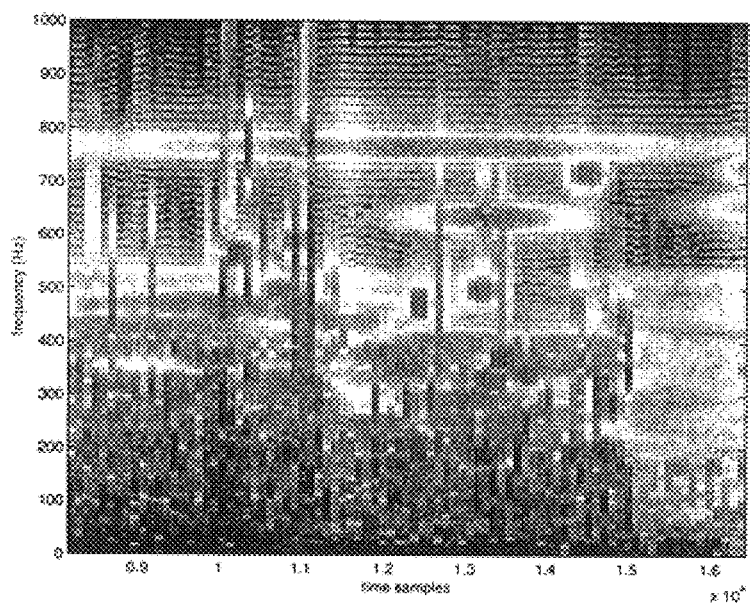
Figure 7:
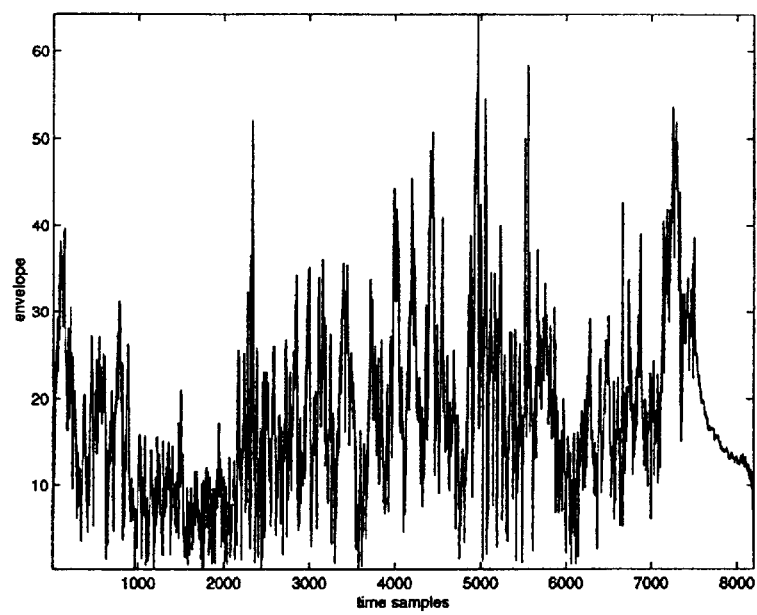
FIG. 7 shows the envelope of the VAG signal shown in FIG. 4.
Figure 8:
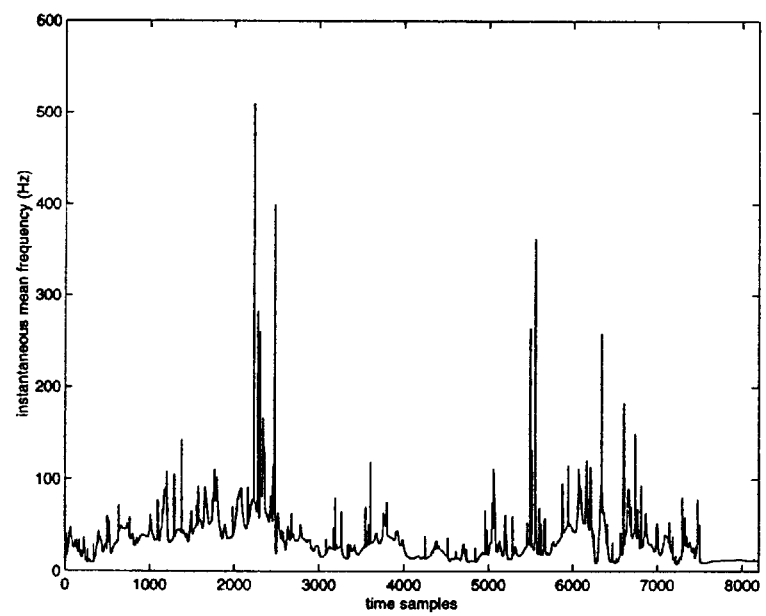
FIG. 8 shows the IMF of the VAG signal shown in FIG. 4, estimated using its OMP TFD.
Figure 9:
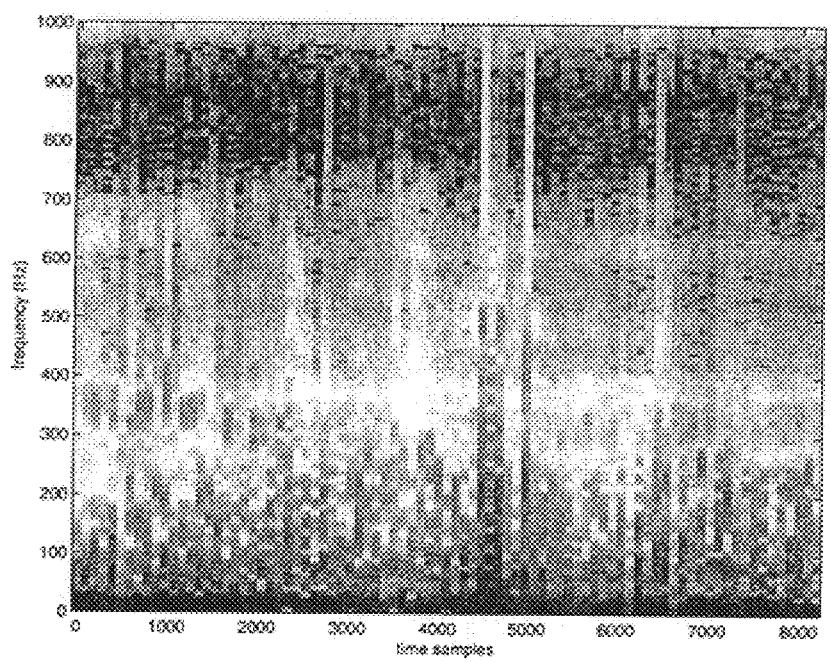
FIG. 9 is a spectrogram of the IMF-based sonified version of the VAG signal shown in FIG. 4. The figure window has been divided into 2 parts to show the time-scale expansion.
Figure 9:
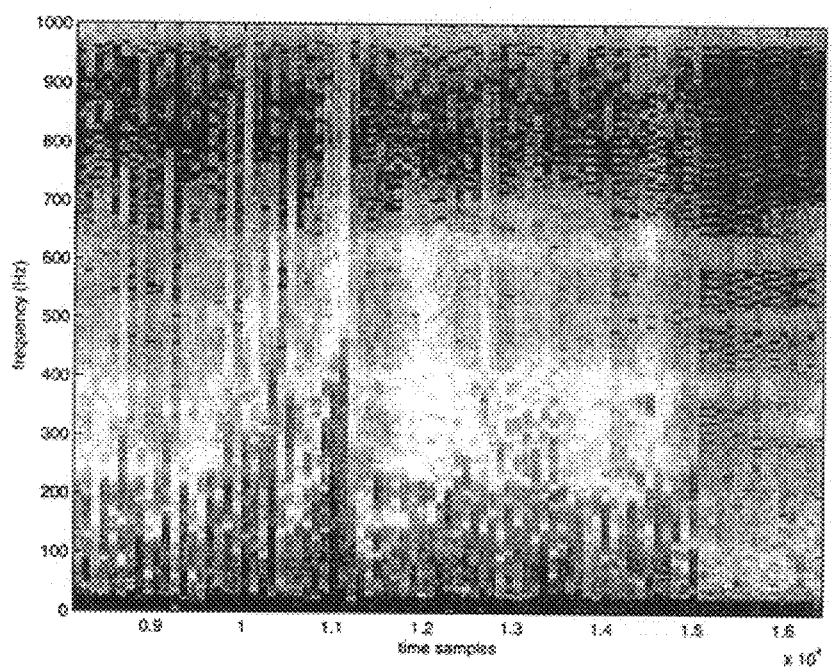

For the sake of illustration, plots of an abnormal VAG signal of a patient with chondromalacia patella grade II and III, and the processed versions of the signal are presented. FIG. 4 shows the original VAG signal and the spectrogram of the signal is shown in FIG. 5. The spectrograms and related entities of the audified and the sonified versions of the signal are shown in FIGS. 6 to 9. The spectrogram of the processed versions clearly indicate the effects of time-scaling when compared to the original spectrogram shown in FIG. 6. The envelope and the IMF of the signal are shown in FIGS. 7 and 8, respectively. The spectrogram shown in FIG. 9 clearly illustrates the envelope-IMF behavior of the sonified signal.

As will be apparent to those skilled in the art, various modifications, adaptations and variations of the foregoing specific disclosure can be made without departing from the scope of the invention claimed herein.

3. References

The following references are referred to above as a numeral within square brackets ([x]). The contents of each such reference is incorporated herein as if reproduced herein in their entirety.

[1] R. A. B. Mollan, G. C. McCullagh, and R. I. Wilson. A critical appraisal of auscultation of human joints. *Clinical Orthopaedics and Related Research*, 170:231–237, 1982.

[2] C. F. Walters. The value of joint auscultation. *Lancet*, 1:920–921, 1929.

[3] M. L. Chu, l. A. Gradisar, and R. Mostardi. A noninvasive electroacoustical evalution technique of cartilage damage in pathological knee joints. *Medical and Biological Engineering and Computing*, 16:437–442, 1978.

[4] G. F. McCoy, J. D. McCrea, D. E. Beverland, W. G. Kernohan, and R. A. B. Mollan. Vibration arthrography as a diagnostic aid in disease of the knee. *Journal of Bone and Joint Surgery*, 69-B(2):288–2931 1987.

[5] Y. Nagata, Joint-sounds in gonoarthrosis—clinical application of phonoarthrography for the knees. *Journal of UOEH*, 10(1):47–58, 1988.

[6] S. Tavathia, R. M. Rangayyan, C. B. Frank, G. D. Bell, K. O. Ladly, and Y. T. Zhang. Analysis of knee vibration signals using linear prediction. *IEEE Trans. Biomedical Engineering*, 39(9):959–970, 1992.

[7] N. P. Reddy, B. M. Rothschild, M. Mandal, V. Gupta, and S. Suryanarayanan. Noninvasive acceleration measurements to characterize knee arthritis and chondromalacia. *Annals of Biomedical Engineering*, 23:78–84, 1995.

[8] Z. M. K. Moussavi, R. M. Rangayyan, G. D. Bell, C. B. Frank, K. O. Ladly, and Y. T. Zhang. Screening of vibroarthrographic signals via adaptive segmentation and linear prediction modeling, *IEEE Trans. Biomedical Engineerings*, 43(1):15–23, 1996.

[9] S. Krishnan, R. M. Rangayyan, G. D. Bell, C. B. Frank, and K. O. Ladly. Adaptive filtering, modelling, and classification of knee joint vibroarthrographic signals for non-invasive diagnosis of articular cartilage pathology. *Medical and Biological Engineering and Computing*, 35:677–684, November 1997.

[10] R. M. Rangayyan, S. Krishnan, G. D. Bell, C. B. Frank, and K. O. Ladly, Parametric representation and screening of knee joint vibroarthrographic signals. *IEEE Trans. Biomedical Engineering*, 44(11):1068–1074, November 1997.

[11] S. Krishnan, R. M. Rangayyan, G. D. Bell, and C. B. Frank. Adaptive time-frequency analysis of knee joint vibroarthrographic signals for non-invasive screening of articular cartilage pathology. *IEEE Transactions on Biomedical Engineering*, 47(6):773, June, 2000.

[12] C. Hayward, Listening to the Earth sing. In G. Kramer, editor, *Auditory Display: Sonification, Audification, and Auditory Interfaces*, pages 369–404. Addison Wesley, Reading, Mass., 1994.

[13] X. Zhang, L.-G. Durand, L. Senhadji, H. C. Lee, and J.-L. Coatrieux. Analysis-synthesis of the phonocardiogram based on the matching pursuit method. *IEEE Trans. Biomedical Engineering*, 45(8):962–971, August 1998.

[14] V. T. Fitch and G. Kramer. Sonifying the body electric: superiority of an auditory over a visual display in a complex, multivariate system. In G. Kramer, editor, *Auditory Display: Sonification, Audification, and Auditory Interfaces*, pages 369–404. Addison Wesley, Reading, Mass., 1994.

[15] T. F. Quatieri, R. B. Dunn, and T. E. Hanna. A subband approach to time-scale expansion of complex acoustic signal. *IEEE Trans. Speech and Audio Processing*, 3:515–519, 1995.

[16] R. M. Rangayyan, A. C. G. Martins, and R. A. Ruschioni, Aural analysis of image texture via cepstral filtering and sonification. *In Proc. SPIE vol. 2656 on Visual Data Exploration and Analysis III*, Pages 283–294, San Jose, Calif., January 1996.

[17] A. C. G. Martins, R. M. Rangayyan, L. A. Portela, E. Amaro Jr., and R. A. Ruschioni. Auditory display and sonification of textured images. *In Proc. Third International Conference of Auditory Display*, pages 9–11, Palo Alto, Calif., November 1996.

[18] P. Meijer. An experimental system for auditory image representation. *IEEE Trans. Biomedical Engineering*, 39(2):112–121, 1992.

[19] D. L. Mansur, M. M. Blattner, and K. L. Joy. Sound graphs: a numerical data analysis method for the blind. *Journal of Medical Systems*, 9(3):163–174, 1985.

[20] D. Malah. Time-domain algorithm for harmonic bandwidth reduction and time scaling of speech signals. *IEEE Trans. Acoustics, Speech, and Signal Processing*, 27(2): 121–133, April 1979.

[21] S. G. Mallat and Z. Zhang. Matching pursuit with time-frequency dictionaries. *IEEE Trans. Signal Processing*, 41(12):3397–3415, 1993.

[22] S. Krishnan. Adaptive signal processing techniques for analysis of knee joint vibroarthrographic signals. *Ph.D. disertation*, University of Calgary, Calgary, AB, Canada, June 1999.

[23] L. Cohen. Time-frequency distributions- A review. *Proc. IEEE*, 77:941–981, 1989.

[24] D. Gabor. Theory of communication. *Proc. IEEE*, 93:429–457, 1946.

[25] B. Boashash. Estimating and interpreting the instantaneous frequency of a signal-Part 1: Fundamentals. *Proc. IEEE*, 80(4):519–538, April 1992.

[26] P. J. Loughlin and B. Tracer. On the amplitude- and frequency-modulation decomposition of signals. *Journal of the Acoustical Society of America*, 100(3):1594–1601, September 1996.

[27] P. J. Loughlin. Comments on the interpretation of instantaneous frequency. *IEEE Signal Processing Letters*, 4(5):123–125, May 1997.

[28] L. R. Rabiner and R. W. Schafer. *Digital Processing of Speech Signals*. Prentice-Hall, Englewood Cliffs, N.J., 1978.

[29] S. Krishnan and R. M. Rangayyan. Automatic denoising of knee joint vibration signals using adaptive time-frequency representations. *Medical and Biological Engineering and Computing*, page in press, 2000.

[30] P. Loughlin, J. Pitton, and L. Atlas, Construction of positive time-frequency distributions. *IEEE Trans. Signal Processing*, 42, 2697–2705, October 1994.

What is claimed is:

1. A method of diagnosing an abnormal joint condition comprising the steps of:
    (a) recording a vibroarthrographic (VAG) signal from the joint as it is in movement;
    (b) directly transforming the VAG signal to an auditory signal; and
    (c) listening to the auditory signal to discern features of diagnostic interest.

2. The method of claim 1 wherein the transformation comprises a manipulation of the VAG signal to produce the auditory signal wherein said manipulation comprises shifting the frequency of all or a portion of the VAG signal and/or shifting the time duration of all or a portion of the VAG signal.

3. The method of claim 2 wherein a time duration shift is accomplished without changing the spectral characteristics of the auditory signal.

4. The method of claim 2 wherein the manipulation comprises both time and frequency scaling by signal decomposition using a matching pursuit algorithm.

5. The method of claim 4 comprising the further step of performing an inverse time and frequency scaling on the auditory signal to verify the scaling step.

6. A method of diagnosing an abnormal joint condition comprising the steps of:
    (a) recording a vibroarthrographic (VAG) signal from the joint as it is in movement;
    (b) extracting features from the VAG signal to control a sound synthesizer;
    (c) generating a sound from the sound synthesizer which is unique to the VAG signal but does not bear a direct relationship to the VAG signal; and
    (d) listening to the sound to discern features of diagnostic interest.

7. The method of claim 6 wherein the feature extraction step comprises the production of an MPTFD or an OMP TFD.

8. The method of claim 6 wherein the sound generation step comprises frequency modulating a sinusoidal waveform with the instantaneous mean frequency of the VAG signal.

9. The method of claim 6 wherein the sound generation step comprises amplitude modulation of a sinusoidal waveform with the absolute value of an analytic version of the VAG signal.

\* \* \* \* \*